(12) United States Patent
Ron et al.

(10) Patent No.: US 6,391,549 B1
(45) Date of Patent: May 21, 2002

(54) MONITORING GENE EXPRESSION

(75) Inventors: Eliora Z. Ron, Tel Aviv; Judith Rishpon, Rehovot; Israel Biran, Beit Herot; Reuven Babai, Kadima, all of (IL)

(73) Assignee: Ramont University Authority for Applied Research & Industrial Development Ltd., Ramat Aviv (IL)

( * ) Notice: Subject to any disclaimer, the term of this patent is extended or adjusted under 35 U.S.C. 154(b) by 0 days.

(21) Appl. No.: 09/283,916

(22) Filed: Apr. 1, 1999

(51) Int. Cl.$^7$ .......................... G01N 33/53; C12Q 1/34; C12Q 1/42; C12N 9/16; C12N 9/26; C12N 5/00; C12N 1/34; C12N 1/20

(52) U.S. Cl. .......................... 435/6; 435/7.91; 435/18; 435/21; 435/196; 435/206; 435/288.5; 435/7.2; 435/325; 435/252.3

(58) Field of Search .............................. 435/7.2, 7.91, 435/18, 6, 21, 196, 201, 288.5, 325, 252.3

(56) References Cited

U.S. PATENT DOCUMENTS 5,149,629 A 9/1992 Rishpon et al. .............. 435/7.9
6,117,643 A * 9/2000 Simpson et al. ............. 435/7.1

OTHER PUBLICATIONS

Scott et al. "Genetically engineered bacteria: electrochemical sensing systems for antimonite and arsenite", (1997) Anal Chem 69:16–20.*

Liverelli et al. "In vivo DNA–protein interactions at the divergent mercury resistance (mer) promoters. I. Metalloregulatory protein MerR proteins" (1993) J Biol Chem 268:2623–2631.*

Karin et al. "Activation of a heterologous promoter in response to dexamethasone and cadmium by metallothionein gene 5'–flanking DNA" (1984) Cell 36:371–379.*

Groskreutz, Debyra and Elaine T. Schenborn, "Reporter Systems," from: Methods in Molecular Biology, vol. 63: Recombinant Protein Protocols: Detection and Isolation, Edited by: R. Tuan Humana Press Inc., pp. 11–30, 1997.

Jain, Vinay K., and Ian T. Magrath, "A Chemiluminescent Assay for Quantitation of β–Galactosidase in the Femtogram Range: Application to Quantitation of β–Galactosidase in lacZ–Transfected Cells," *Analytical Biochemistry*, v. 199, pp. 119–134 (1991).

Kulys, J. V. Razumas and A. Malinauskas, "297–Electrochemical Oxidation of Catechol and p–Aminophenol Esters in the Presence of Hydrolases," Bioelectrochemistry and Bioenergetics v. 7, pp. 11–24 (1980) J. Electroanal. Chem. V. 116, pp. 11–24 (1980).

Másson, M. et al., "Immunosensing with amperometric detection, using galactodidase as label and p–aminophenyl–β–D–galactopyranoside as substrate," *Analytica Chimica Acta* v. 304, pp. 353–359 (1995).

"Unit 3 The lac System, B–Galactosidase Assay," *Procedures for Working With lac*, pp. 72–74, 1992.

Rosen, I. and J. Rishpon, "Alkaline Phosphatase as a label for a heterogeneous immunoelectrochemical sensor, An electrochemical study," *J Electroanal. Chem.*, v. 258, pp. 27–39 (1989).

Silhavy, Thomas J., amd Jonathan R. Beckwith, "Uses of lac fusions for the Study of Biological Problems," *Microbiological Reviews*, v. 49, No. 4, pp. 398–418 (Dec. 1985).

Weichart, Dieter et al., "Identification and characterization of stationary phase–inducible genes in *Escherichia coli*," *Molecular Microbiology*, v. 10(2), pp. 407–420 (1993).

Yim, Harry H. and Merna Villarejo, "osmY, a New Hyperosmotically Inducible Gene, Encodes a Periplasmic Protein in *Escherichia coli*," *Journal of Bacteriology*, v. 174, No. 11, pp. 3637–3644 (Jun. 1992).

* cited by examiner

*Primary Examiner*—Rebecca E. Prouty
*Assistant Examiner*—David J. Steadman
(74) *Attorney, Agent, or Firm*—Nath & Associates PLLC; Gary M. Nath; Todd L. Juneau

(57) ABSTRACT

A method and system for detecting a parameter of a host cell, a cell culture or medium is provided. A host cell is transfected with an expressible DNA sequence which is under expression control of an inducible promoter sequence. The promoter sequence is inducible in correlation with the parameter, the expressible sequence encoding an enzymatically active product which can catalyze a reaction giving rise to an electrical signal which is detectable in an electrochemical measurement. An electrical signal determined in an electrochemical system then serves as an indication for the parameter.

25 Claims, 10 Drawing Sheets

MONITORING GENE EXPRESSION

FIELD OF THE INVENTION

The present invention relates to a method, system and kit for use in monitoring of DNA expressions within cells.

PRIOR ART

The following is a list of references which are intended for a better understanding of the background of the present invention:

REFERENCES

Groskreutz, D. and Schenborn, E. T., Reporter systems. In: Methods in molecular biology, Vol. 63: Recombinant protein protocols; detection and isolation. R. S. Tuan (ed.), pp. 173–218, Humana Press Inc., Totowa, N.J.

Jain, V. K. and Magrath, I. T., A chemiluminescent assay for quantitation of β-galactosidase in the fentogram range: application to quantitation of β-galactosidase in lacZ-transfected cells, *Anal. Biochem.,* 199:119–124 (1991).

Kulys, J., Razumas, V and Malinauskas, A., Electrochemical oxidation of catechol and p-aminophenol esters in the prsence of hydrolase, *J. Electroanal. Chem.* [*Bioelectrochem. Bioenerg.* 7] 116.11–24 (1980).

Masson, M., Liu, Z., Haruyama, T., Kobatake, E., Ikariyama, Y and Aizawa, M., Immunosensing with amperometric detection, using galactosidase as label and p-aminophenyl-β-D-galactopyranoside as substrate. *Anal. Chim. Acta* 304;353–359 (1995).

Miler, J. H., A short course in bacterial genetics, p. 72–74, Cold Spring Harbor Press., Cold Spring Harbor, N.Y. (1992).

Rosen, I. and Rishpon, J., Alkaline phosphatase as a label for heterogeneous immunoelectrochemical sensor, *J. Electroanal. Chem.,* 258:27–39 (1989).

Silhavy, T. J. and Beckwith, J. R., Uses of lac fusions for the study of biological problems, *Microbiol. Rev.* 49;398–418 (1985).

U.S. Pat. No. 5,149,629.

Weichart, D., Lang, R., Henneberg, N., & Hengge-Aronis, R., Identification and characterization of stationary phase-inducible genes in *Escherichia coli. Mol. Microbiol,* 10:407–420 (1993).

Yin, H. H. and Villarejo, M., OsmY, a new hyperosmotically inducible gene, encodes a periplasmic protein in *Escherichia coli., J. Bacteriol.* 174:3637–3644 (1992).

BACKGROUND OF THE INVENTION

Reporter gene systems are used in gene expression studies and for biosensor developmont, Various analytical methods are available for monitoring the protein expressed by a reporter gene. These methods include photometry, radiometry, fluorescence, colorimetry and immunoassays (Groskreutz, D. et al., 1997). A light emitting gene was also used as the reporter gene and several techniques have been developed to monitor the light emitting from the cells (Legocki, R. P. et al., 1993).

The predominantly used methods for the identification and quantification of the reporter gene products in cell cultures involve repeated samplings of the culture and an assay for the enzymatic activity, that often involves an additional step of lysis or permeabilization of the cell and must be performed under aerobic conditions. These procedures perturb the culture and are time consuming at times, providing results only after several hours.

The gene lacZ, coding for the *Escherichia coli* enzyme β-galactosidase is one of the most widely used reporter genes (Silhavy & Beckwith, 1985) and has been used in colorimetric assays (Miler, 1992), or using fluorometry or chemilluminometry (Jain & Magrath, 1991). These methods involve the permeabilization of the cells followed by a multi-step procedure.

The enzymatic activity of β-galactosidase can be determined electrochemically by using the substrate p-aminophenyl-β-D-galactopyranoside (PAPG). The product of the enzymatic reaction, p-aminophenol (PAP) is oxidized at an electrode.

Several electroanalytical methods for PAP detection have been reported (Kulys & Malinauskas, 1980; Masson et al, 1995). An electrochemical imunoassay, in which a constant potential is applied on the electrode and the current generated by the oxidation of PAP is measured was also described (U.S. Pat. No. 5,149,629).

GENERAL DESCRIPTION OF THE INVENTION

In accordance with the present invention novel means are provided for monitoring of gene expression within cells. As will be detailed further below, the invention may be used for determination of cell parameters in a cell culture, for cell biology research, for determining parameters or conditions of a sample, etc. as well as for biosensor development.

In accordance with one aspect, the present invention provides a method for detecting a parameter of a host cell, comprising:

(a) transfecting said cell with an expressible DNA sequence under expression control of an inducible promoter sequence, said promoter sequence being inducible in correlation wit said parameter, said expressible sequence encoding an enzymatically active product which can catalyze a reaction giving rise to an electrical signal which is detectable in an electrochemical measurement;

(b) placing the transfected cells in an electrochemical cell; and (c) measuring the level of the electrical signal, a signal above a threshold level indicating the presence of said parameter.

The present invention also provides a method for determining a parameter of a medium, comprising:

(a) providing cells transfected with an expressible DNA sequence under expression control of an inducible promoter sequence, said promoter sequence being inducible in correlation with said parameter, said expressible sequence encoding an enzymatically active product which can catalyze a reaction giving rise to an electrical signal which is detectable in an electrochemical measurement;

(b) placing said cells in the medium or a sample thereof; and (c) providing an electrochemical cell and measuring level of said electrical signal, the level of said signal being correlated to the level of said parameter.

Still further provided by the invention is a method for monitoring a growth status parameter, said parameter being a parameter characteristic of a defined growth or cell cycle phase or a defined culture phase of a cell culture, comprising:

(a) providing a culture of cells, wherein at least some of the cells are transfected with an expressible DNA sequence under expression control of an inducible promoter sequence, said promoter sequence being inducible in correlation with the growth status parameter, said expressible sequence encoding an enzymatically active product which can catalyze a reaction giving rise to an electrical signal which is detectable in an electrochemical measurement;

(b) in an electrochemical cell, continuously or periodically measuring said electrical signal, said signal being indicative of said growth status parameter.

By a further of its aspects the present invention provides a system for monitoring expression of a target promoter, comprising:

(a) an electrochemical cell;
(b) cells transfected with an expressible DNA sequence under expression control of said target promoter, said expressible sequence encoding an enzymatically active product which can catalyze a reaction giving rise to an electrical signal which is detectable in an electrochemical measurement; and
(c) apparatus for measurement of said electrical signal.

By a still further aspect the present invention further provides a kit for use in detecting a parameter of host cell, a medium parameter or a cell or cell culture growth stats indicator parameter, comprising:

(a) host cells transfected wit an expressible DNA sequence under expression control of an inducible promoter sequence, said promoter sequence being inducible in correlation with said parameter, said expressible sequence encoding an enzymatically active product which can catalyze a reaction giving rise to an electrical signal which is detectable in an electrochemical measurement;
(b) at least one component of an electrochemical cell, said electrochemical cell being adapted for receiving and holding the host cells and for performing said electrochemical measurement.

GLOSSARY

The following is an explanation of some terms used above and in the following description and claims:

Parameter—when applied to a cell, referring to a certain property of interest within the cell which may include a certain phase of the cell cycle, a response of the cell to stimulants existing in an extracellular medium or a change in the expression of any gene (such stimulants may include a certain environmental pollutant, toxic chemical nutritional substance, existence of a substance which regulates cell activity or growth, production of certain substances within the cell, etc.). When applied to a medium—referring to the existence in medium of substances or a condition (e.g. temperature, ionic strength, etc.) which affects cellular parameters in a host cell.

Host cell—a cell which is transfected with a DNA construct in accordance with the invention. Various kinds of host cells may be used as described below.

Enzymatically active product—a product of gene expression which can perform an enzymatic activity. Such a product may be an enzyme per se, typically active within the cell, or may be an enzyme having a signal peptide or protein, (e.g. an expression product having an expressible DNA sequence obtained by fusing a sequence encoding the enzyme and a sequence encoding the signal, peptide or protein).

Electrochemical measurement—a measurement performed by the use of electrodes in a solution, typically in an electrochemical cell. The measurement may be performed, for example, by chrono-amperometry, chrono-potentiometry, cyclicvoltometry, chrono-coulometry or square wave voltometry. A signal detectable in such a measurement, is one that differs in such electrochemical measurement from the control.

Medium—any medium, which may be a liquid, a solid, or a gas in which a certain quality is to be measured. Such a quality may be the existence of a certain substance in the medium, a temperature of the medium, etc. Where the medium is an aqueous liquid, it can be applied as such onto the host cells. Where the medium is a gas or a solid, it has to be first mixed with a liquid medium which will then be applied onto the host cells. Alternatively, a gas medium may be bubbled through a liquid medium comprising a culture of the host cells. Similarly, a solid substrate, such as soil, may also be admixed with a medium containing a culture of the tested cells.

Correlation/correlated—refers to the correlation between the measured signal and the parameter which is to be determined. Such correlation may be manifested either by a proportional increase in the signal in line with the level of said parameter, or a proportional decrease in the signal in line with said parameter.

Growth status—a term referring particularly to a culture of cells. A growth status may be an algorithmic growth phase of the culture, a stationary phase, etc.

Determination/determining—including a qualitative determination of existence or of non-existence of a certain parameter or condition as well as a qualitative determination of the level of such parameter or condition. The parameter which is determined may for example be the existence of the certain substance in the medium or cell as well as a quantitative determination of its level.

BRIEF DESCRIPTION OF THE DRAWINGS

In order to better understand the invention, reference will at times be made to the annexed drawings, in which.

DETAILED DESCRIPTION OF THE INVENTION

Figure 1:
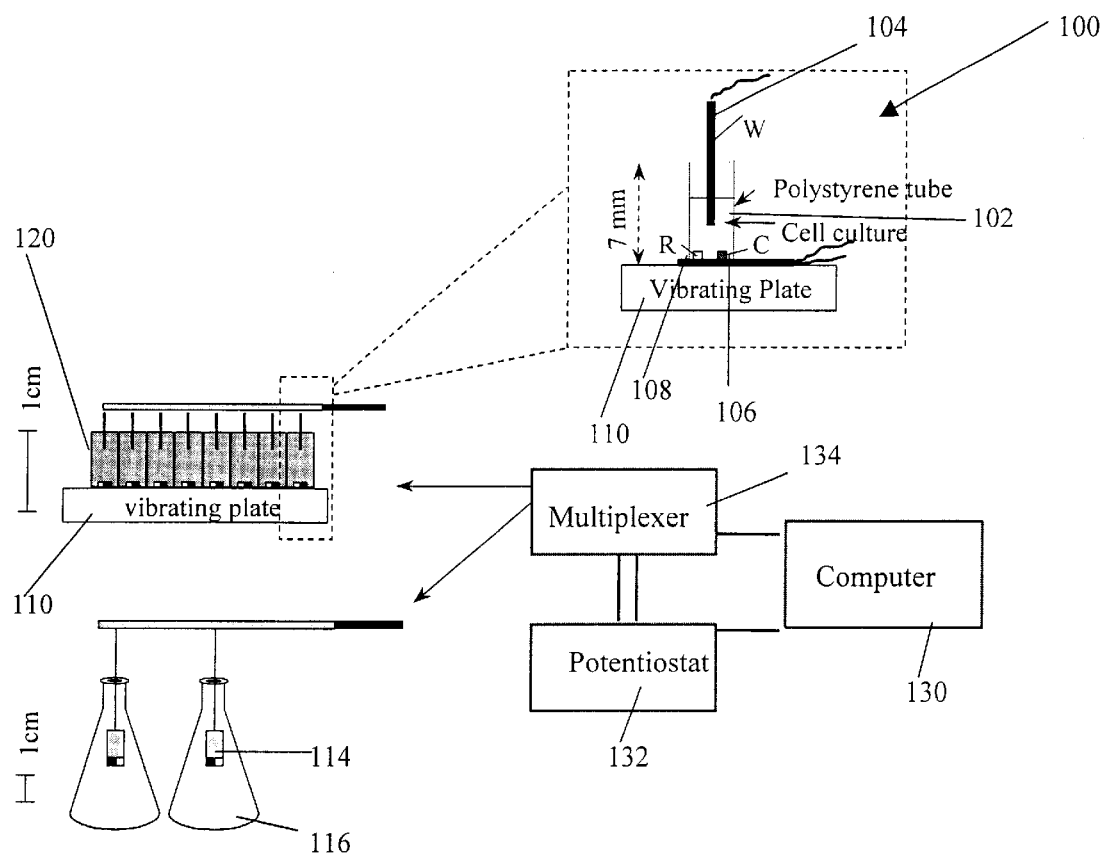
FIG. 1 is a schematic illustration of a computerized electrochemical system in accordance with the invention.

In accordance with the present invention a novel whole cell assay is provided. As distinct from prior art methods, in accordance with the invention it is not required to disrupt the integrity of the cells used in the assay prior to measurement, and there is no need for preparatory steps prior to performance of the assay. Rather, in accordance with the invention, a cell sample is placed in an electrochemical cell, or alternatively, the electrochemical cell is formed within the culture medium itself. The nature of the whole cell assay of the invention enables to perform the desired measurements in the cell medium in which the cells are regularly grown in rather than in a specifically fitted buffer which is required in prior art methods.

In accordance with the invention the assay is also very rapid due to a very short incubation time required until obtaining results.

The assay of the invention is useful to determine the activity of almost any type of inducible promoter using a variety of expressible DNA sequences as "reporter genes".

In accordance with the invention, host cells are used which are transfected with a DNA construct which comprises said expressible DNA sequence under expression control of a promoter.

The host cell may be any cell in which said expressible DNA sequence can be expressed. Host cells may be prokaryotic and eukaryotic cells, include, for example, bacterial cells, mycoplasma, yeast cells, protazoa, insect cells, mammalian cells, particularly human cells, etc.

The host cells may be in suspension or may he immobilized. The cells may also be fixed to a substrate such as, for example, various gels, various solid matrices, the electrode itself, etc. The cells may be fresh cells, or may be cells which have been frozen and thawed.

Transfection of the cells may be achieved by any known transfection techniques. Such techniques may involve the use of viral vectors such as, for example, the *baculla* virus system for the transfection of insect cells, the adenovirus system for transfection of human cells, *lambda* bacterial system for transfection of bacteria, etc. In addition, a variety of transfection techniques involving the use of plasmids may also be used for transfection of the host cells. A typical method of transfection of mammalian cells may be the calcium chloride technique ionophoretic transfection techniques, etc. (Sambrook, J., Fritsch, E. F., and Maniatis, T., Molecular cloning: a laboratory manual (second edition) Cold Spring Press, Cold Spring Harbor, N.Y. (1989)). As will be appreciated, the invention is not limited to a particular host cell or to the type of transfection method utilized. The artisan should have no difficulties of choosing a specific host cell for use in a specific assay and of choosing the most appropriate transfection technique in each case.

The promoter included in the DNA construct in which the cell is being transfected may be selected from a wide variety of known promoters. The requisite of the promoter is that it will be inducible in the host cell upon occurrence of the parameter which is to be determined. For example, the promoter may be such which is inducible at a specific phase of the cell cycle, it may be inducible in the presence of a certain substance in the cell, e.g. a nutritional substance or a regulatory substance, external toxic chemical or pollutant, it may be a promoter inducible by external culture conditions, e.g. when the culture reaches a stationary growth stage, or by an external factor such as a toxic chemical, a pollutant, etc.

The promoter which is used may be an autologous promoter, namely a promoter which naturally controls expression of the expression DNA sequence, or may be a heterologous promoter which was fused to the expressible DNA sequence.

The expressible DNA sequence encodes a catalytically active expression product. In accordance with one embodiment, such an expression product is an enzyme which catalyzes a reaction giving rise to a product which is permeable or which can be transported through the cell membrane and which can then undergo redox reaction at one of the electrodes of the electrochemical cell. Example of such an enzyme is β-galactosidase, which can catalyze a reaction in which the p-aminophenyl-β-D- galactopyranoside (PAPG) is convened into p-aminophenol (PAP). PAP can be transported through the cell membrane and then oxidized at the electrode by the following chemical reaction:

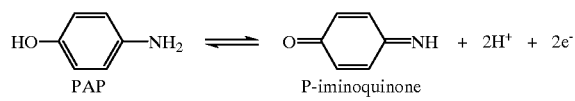

$$\text{HO}-\!\!\!\left\langle\!\!\!\begin{array}{c}\\ \end{array}\!\!\!\right\rangle\!\!\!-\text{NH}_2 \rightleftharpoons \text{O}=\!\!\!\left\langle\!\!\!\begin{array}{c}\\ \end{array}\!\!\!\right\rangle\!\!\!=\text{NH} + 2\text{H}^+ + 2\text{e}^-$$

PAP                P-iminoquinone

Other non limiting examples of enzymes and relevant substrates include; The enzyme alkaline phosphatase (AP) or the enzyme secreted alkaline phosphatase (SEAP) with the substrate PAPP (p-aminophenol-phosphate) or when using the enzyme glocuse oxidase immobilized to the electrode the substrate can be glocuse-6-phosphate, the enzyme chloramphenicol acetyl transferase (CAT) and the substrate chloramphhenicol, the enzyme b-glucuronidase and any glycosaminoglycans or other glycoconjugates that after the removal of the b-glucorunic acid residue become electrochemicaly active.

The expressible DNA sequence may be a sequence encoding a product which can naturally be expressed in the host cell, or may be a product heterologous to the cell.

The expression product may also be an enzyme construct which is transported out of the cell and becomes active extracellularly after secretion. Such an expression product may, for example, be a secreted protein fused to the "tag" enzyme alkaline phosphatase (Manoil et al., 1990).

In accordance with one embodiment of the invention, the reporter gene may comprise several genes of which one encodes the substrate or a peptide capable of producing the substrate and another gene encodes the enzyme capable of catalyzing a reaction on the produced substrate. Several reporter genes may be expressed from the sane promoter, one of the reporter genes encoding the substrate. In this manner, it is not necessary to add a substrate to the cells and the final signal is actually the result of a sequence of proteins in the complex.

In accordance with one embodiment the entire culture consists of the host cells which also produce a substance of interest as well as being capable of expressing said expressible product thus allowing to monitor said parameter. In accordance with another embodiment, the culture comprises a certain proportion of the host cells which allow to monitor said parameters. In such an embodiment, it is necessary to continuously ascertain that a fixed proportion between the host cells and the culture cells are maintained. Furthermore, in accordance with this embodiment, it is possible, at times, to include in the culture a number of different host cells, each expression a different expressible product to allow to differentiate between the different parameters.

The determination of the parameters may, by one embodiment (the "on-line" embodiment), be performed by forming the electrochemical cell within the fermentation vessel. This will require to include in such a vessel typically three electrodes, a reference electrode, a working electrode and a counter electrode.

Alternatively, rather than performing the measurement within the culture, by an additional embodiment the "semi on-line" embodiment) it is possible also to continuously withdraw samples and place such samples within the electrochemical cells. In case where the culture contains different host cells, in each electrochemical cell, it is possible to add a different substrate to allow to differentiate between the signals from different types of host cells.

The present invention may have a variety of applications. Some embodiments will now be described in some detail:

1, Monitoring Status of a Culture

A large number of bacteriological processes involve culturing of cells to obtain products produced by the cells. In such fermentation processes various conditions have to be determined continuously which include the exact availability of a nutrient in the fermentor, the state of the culture, namely whether it is an algorithmic growth phase or a stationary phase, and especially the concentration of the required fermentation product at any given time. The present invention provides a novel way for monitoring such parameters.

2. Determining a Tested Medium

The tested medium may be a biological medium such as a body fluid, e.g. whole blood or plasma, may be an environmental sample, e.g. a sample obtained from a water reservoir, may be a soil sample, etc. Where for example it is desired to determine the existence of a certain substance in the sample, the sample may first be treated for extraction of such a substance and the fraction containing substance is then admixed with the culture medium comprising the host cell. It is obviously also possible to admix the sample directly into the culture, which may be advantageous, particularly in field applications, in terms of simplicity and speed of assay.

Where the medium to be determined is a gas, there is typically an initial phase of bubbling the gas through the host cell—comprising culture medium.

One potential use of the method is to determine contamination of different media with toxic substances, e.g. determining contamination of soil samples or water reservoirs with mercury, or cadmium.

In each case, the host cells will be designed such that the substance or condition of interest will induce the promoter, whereby said expressible product will be expressed by the host cells. An added substrate will then give rise to a product which will yield the electrical signal, indicative of the presence of the substance of interest in the sample.

In accordance with one embodiment, it is possible to use an electrode array which comprises a number of electrodes on a very small area. Each electrode may contain a different host cell so that each host cell on the array is capable of reacting to a different tested parameter. The various host cells may comprise different promoters, they may comprise different reporter genes, different substrates may be used or there may be a combination of any of the above. In this manner, by using a miniaturized electrode array a large number of measurements may be carried out simultaneously on one or more tested samples.

3. Assay System and Technique

As shown in FIG. 1, each electrochemical cell 100 comprises a vessel 102, a measurement electrode 104, a return electrode 106 and a reference electrode 108. The cells are typically placed on a vibrating plate 110 for continuous thorough mixing of the contents of the cells.

The working electrode 104 may be of a variety of different kinds, for example, it may be made of carbon, including glassy carbon, activated carbon cloth electrode, carbon felt, platinized carbon cloth, plain carbon cloth), may be made of gold, platinum or silver. The counter electrode may also be made of the same material as the working electrode. The reference electrode may for example be saturated calomel electrode, may be an Ag/AgCl electrode. Furthermore, the electrodes may be of a screen printed electrode 114 which can be inserted into a cell culture vessel 116 without the need to withdraw a sample and transport it into a separate electrochemical cell.

The electrochemical cell 100 shown in FIG. 1, is a three-electrode cell. As will be appreciated, it is possible also to use a two-electrode cell, The electrochemical cells are typically provided as an array 120 comprising a plurality of such cells.

The system further comprises a control module which may be a computer 130, a potentiostat 132 and a multiplexer module 134 which is needed in case of a typical embodiment for simultaneous measurement from a plurality of electrochemical cells.

The electrochemical measurement performed in the cell will now be described in reference to the chrono-amperometric mode. As will be appreciated, it applies, *mutatis, mutandis* also to the other electrochemical measurement modes mentioned above. Furthermore, the description will be made with reference to the use of a multi-electrode system (the system comprising an may of electrodes) and it is clear that it applies to a system comprising a single cell as well.

In the beginning of the electrochemical measurement all the electrodes are operated together, and the computer scans all the electrodes via the parallel port, and the background response to the potential application of each electrode is recorded by the computer. The entire electrochemical measurement sequence can be performed over a long period of time while measuring the currents resulting from the changes in the concentration of the products. In cases where the electrodes' surfaces are not identical due to natural variability, the system can be calibrated by measuring the oxidation or reduction of an electroactive species, typically the same species which is the product of the enzymatic reaction in the electrochemical cell and comparison of the results of all the electrodes.

In performing the assay, the electrodes may be connected to the potentiostat and at the same time also collected via the multiplexer to a parallel port of the microcomputer.

Each electrode is inserted in an electrochemical cell containing a reference electrode and a counter electrode which are also connected to the potentiostat. A specific potential is applied by the potensistat on the electrodes (which can be the same for all the electrodes or can be a different potential to each electrode) and the current in each electrode is detected. The electrical signals are visualized in real-time on the computer screen.

4. Electrodes

The electrodes in the system of the invention may be reusable electrodes or disposable ones. Reusable electrodes may for example be electrodes made of glassy carbon in a disk or rod shape which are embedded in teflon. Disposable electrodes may for example be electrodes in the form of carbon paper, carbon cloth, carbon felts, or the screen printed electrode of the kind noted above.

5. Kit

The kit which may be used in accordance with the invention comprises host cells transfected wit an expressible DNA sequence under expression control of an inducible promoter sequence as described above. The promoter sequence used will depend on the parameter to be determined using the kit. Thus, for example, if the kit is used for detection of environmental pollutants in the form of heavy metals such as cadmium, the kit will comprise cells transfected with a promoter which is inducible in the presence of low concentrations of cadmium. The expressible DNA sequence in the cells may be any sequence which encodes an enzymatically active product that can catalyze a reaction giving rise to an electrical signal which is detectable in an electrochemical measurement. For the electrochemical measurement the kit also comprises electrodes, optimally in an electrochemical cell. Wherein the substrate of the enzymatically active product present in the cells of the kit is not endogenous to the cells, the kit will also comprise a substrate which is enzymatically reacted on by the enzymes to yield the reaction product giving rise to a redox reaction at an electrode of the electrochemical cell.

The kit also comprises at least one component of an electrochemical cell, said electrochemical cell being adapted for receiving and holding the host cells and for performing said electrochemical measurement. The at least one component is typically at least a substrate for holding the cells. Such a substrate may be a measuring electrochemical electrode of the cell, may be a carrier substrate for placing in the electrochemical cell, etc. In addition, the kit may at times comprise all cell components, either already assembled in a manner to allow immediate use of the electrochemical cell for performing the measurement, or at times disassembled, In accordance with one embodiment, the kit may comprise an array of electrodes, each holding a differently transfected host cell that is thus suitable for detecting a different parameter, such as the array described above.

Where the kit is used for on-line and in situ monitoring of a parameter, mainly an environmental parameter, the host cells and electrochemical cells are preferably in the form of a small portable device which is simple for handling and transferring to the location wherein the parameter is to be determined.

The above kit may be easily attached to means which can record the measured signal and if desired, process the results (e.g. a mini computer as described above).

EXAMPLES

The examples will now be illustrated by the following non-limiting examples with occasional reference to the attached figures:

Materials and Methods

Bacterial strains and growth. $E.\ coli$ K-12 strain K10 (Hfr, tonA22, ompF626, relA1, pit10, spoT1, $T2^R$ CGSC [Coli Genetic Stot Center, New Haven, Conn.] 4234) was from the lab collection, Strains $E.\ coli$ RO151 (MC4100 φ(csi-5::lacZ) and $E.\ coli$ RH99 (RO151 rpoS359::Tn10) were described before (Weichart et. al., 1993). All cultures were grown aerobically at 37° C. with vigorous shaking in LB media (Miler, 1992), supplemented, when required, with 5 μg/ml of tetracycline or 25 μg/ml of kanamycin.

Enzyme and chemicals, p-aminophenyl-β-D-galactopyranoside (PAPG), isopropyl-β-D-thiogalactopyranoside (IPTG) and β-galactosidase (β-D-galactoside galatohydrolase; EC 3.2.1.23) were obtained from Sigma Chemicals Company (St Louis, Mo.).

The amperometric assay. Electrochemical measurements were performed using a disposable three-electrode cell, based on a screen-printed electrode (total volume of 0.3 ml). The electrochemical cells were made of polystyrene tubes (FIG. 1). Graphite ink was used as the counter electrode and Ag/AgCl ink were the reference electrodes. Disposable graphite electrodes in cylindrical form (made from pencil leads, HB 0.9 mm) were used as the working electrodes. The assay was performed directly in the electrochemical cells which were vibrated to achieve mixing. The same screen-printed electrodes and graphite working electrode were also used for direct measurements in cultures. In this case the electrodes were placed inside the Erlenmeyer flask as shown in FIG. 1 and mixing was achieved by bubbling air. The graphite electrode was held at 220 mV versus the reference electrode and the substrate PAPG concentration was 0.4 mg/ml.

Figure 2:
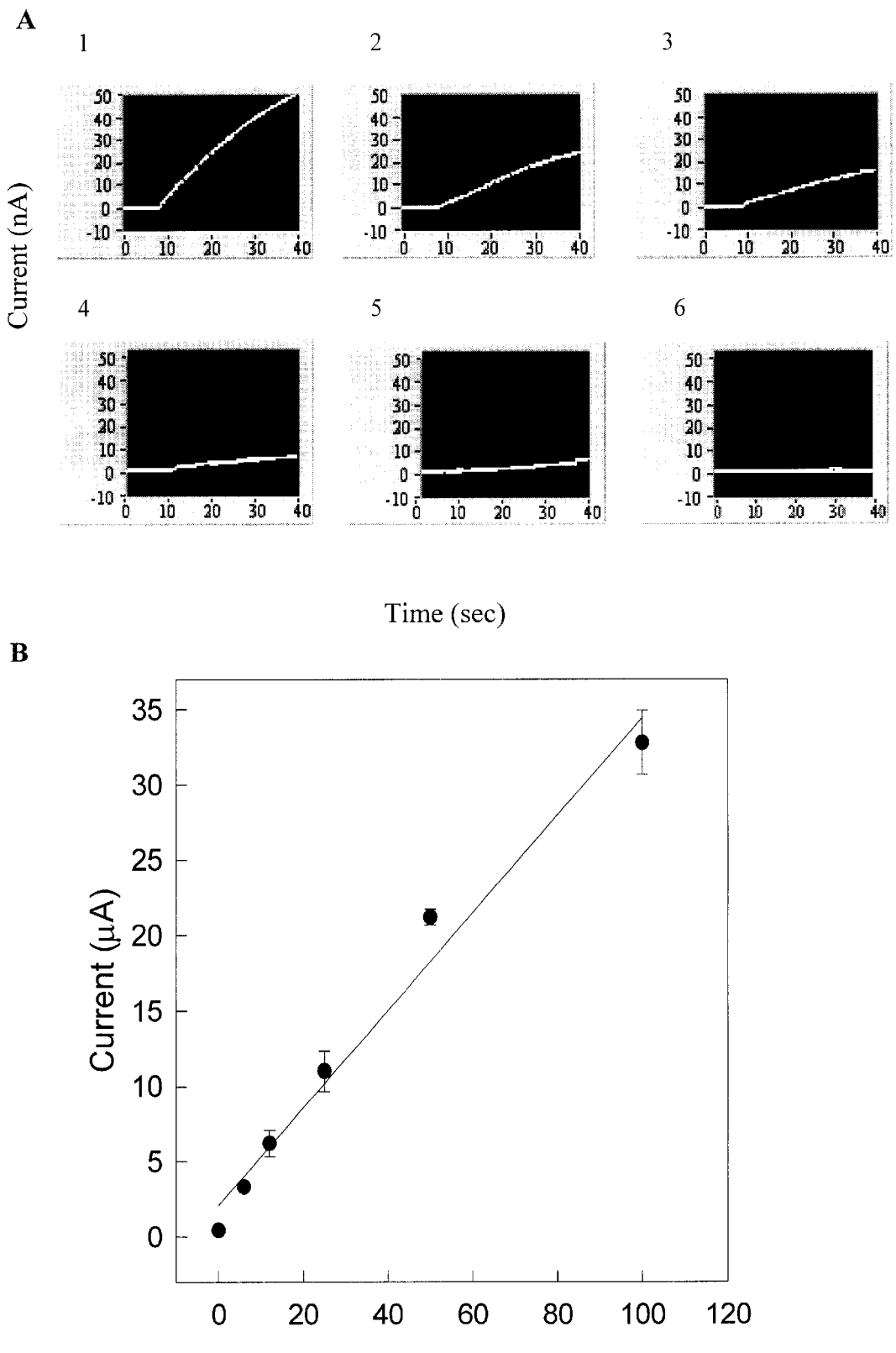
FIGS. 2A–B shows the on-line monitoring of β-galactosidase added to the medium in different concentrations: (1) 100 units/ml; (2) 50 units/ml; (3) 25 units/ml; (4) 12 units/ml, (5) 6 units/ml, (6) no enzyme added.
Figure 3:
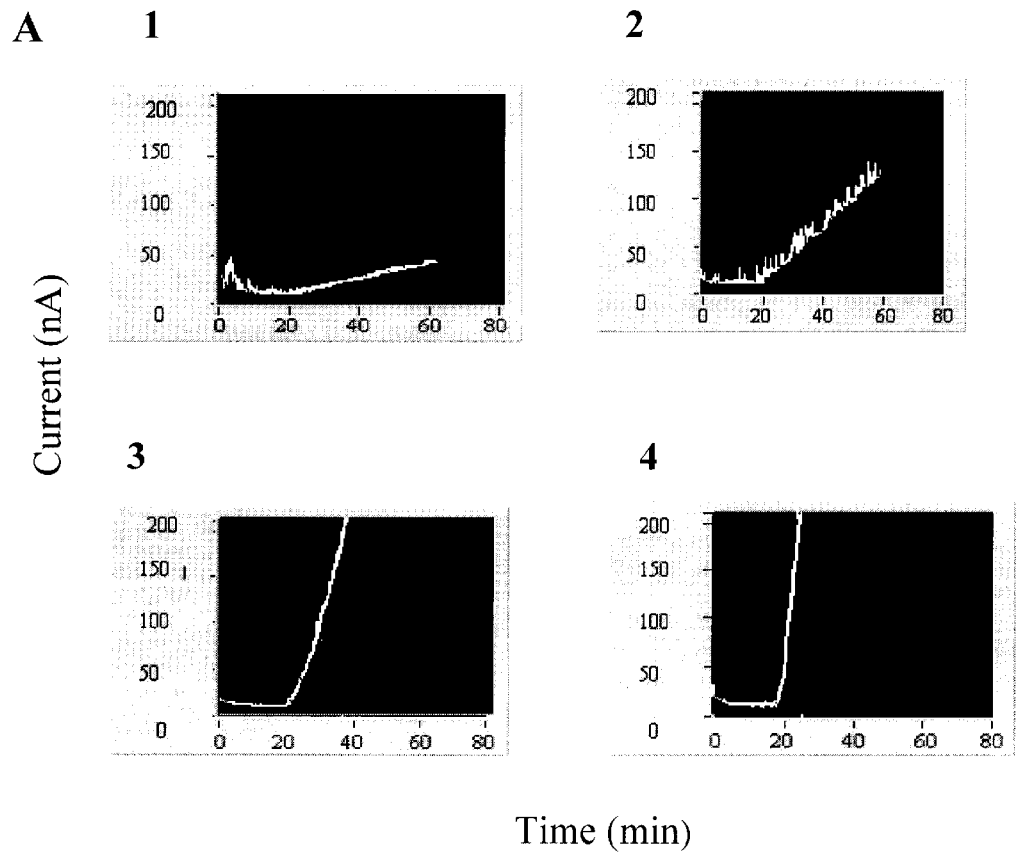
FIGS. 3 A–B shows the monitoring of β-galactosidase activity of E. coli cultures treated with increasing concentrations of IPTG: (a) no IPTG, (b) 0.5 $\mu$M IPTG, (c) 5 $\mu$M IPTG, (d) 50 $\mu$M IPTG.
Figure 3:
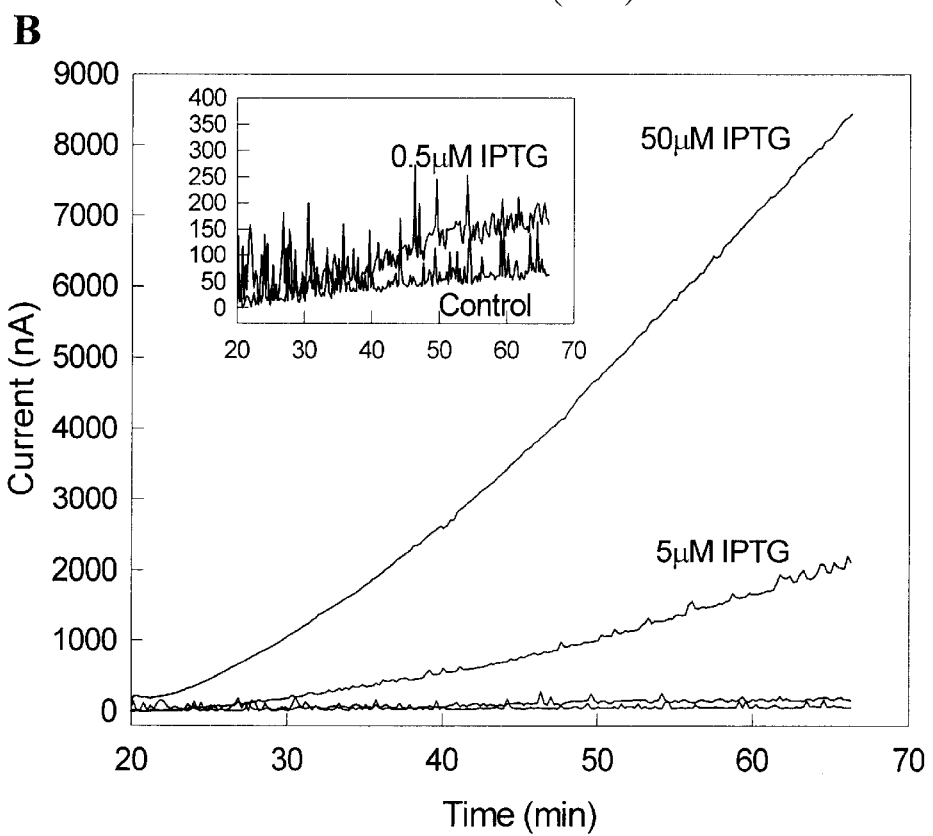

The experimental setup. The electrochemical measurements were performed using a PAR VersaStat potentiostat connected to 8 channel PAR 314 Model multiplexer (EG&C Princeton Applied Research, Princeton, N.J.). This system allows simultaneous measurements of eight samples with disposable electrochemical cells. The measurements were controlled by a LAbVIEW-based software using a Windows 95 operating system. The electrical current from the activity of β-galactosidase was visualized simultaneously in all eight samples in real-time on the computer screen (FIG. 2 and FIG. 3).

Results

Example 1

Configuration and Optimization of the LacZ (β-galactosidase) Amperometrie Monitoring System A multiple-cell electrochemical device as described above was used for optimizing the detection of β-galactosidase activity. The results presented in FIG. 2A demonstrates the use of the multiple-cell device for determining the activity of purified β-galactosidase, using PAPG as a substrate. The results are presented as visualized on the computer screen and represent the signals from the enzymatic reaction in six electrochemical cells containing increasing concentrations of the enzyme as can be seen in FIG. 2B. In the calibration plot constructed from these and additional data a linear correlation was observed in the range of 3 to 100 units/ml and the detection limit was 1 unit/ml of β-galactosidase.

Example 2

On-line Monitoring of the lacZ Reporter Gene Product β-galactosidase in Intact Bacteria An on-line electroanalytical assay for β-galactosidase was used where the enzymatic activity was determined following induction with IPTG. Increasing concentrations of the inducer were added to cultures of $E.\ coli$ K10 (Annette & Anthony, 1987) and the current signal was monitored on-line in all the cultures simultaneously (FIG. 3A). As can be seen in FIG. 3B he slope of the current signals with time was proportional to the concentrations of IPTG added (from 0.5 μM of IPTG).

Example 3
Monitoring the Onset of Stationery Phase in *Escherichia E.coli*

Figure 4:
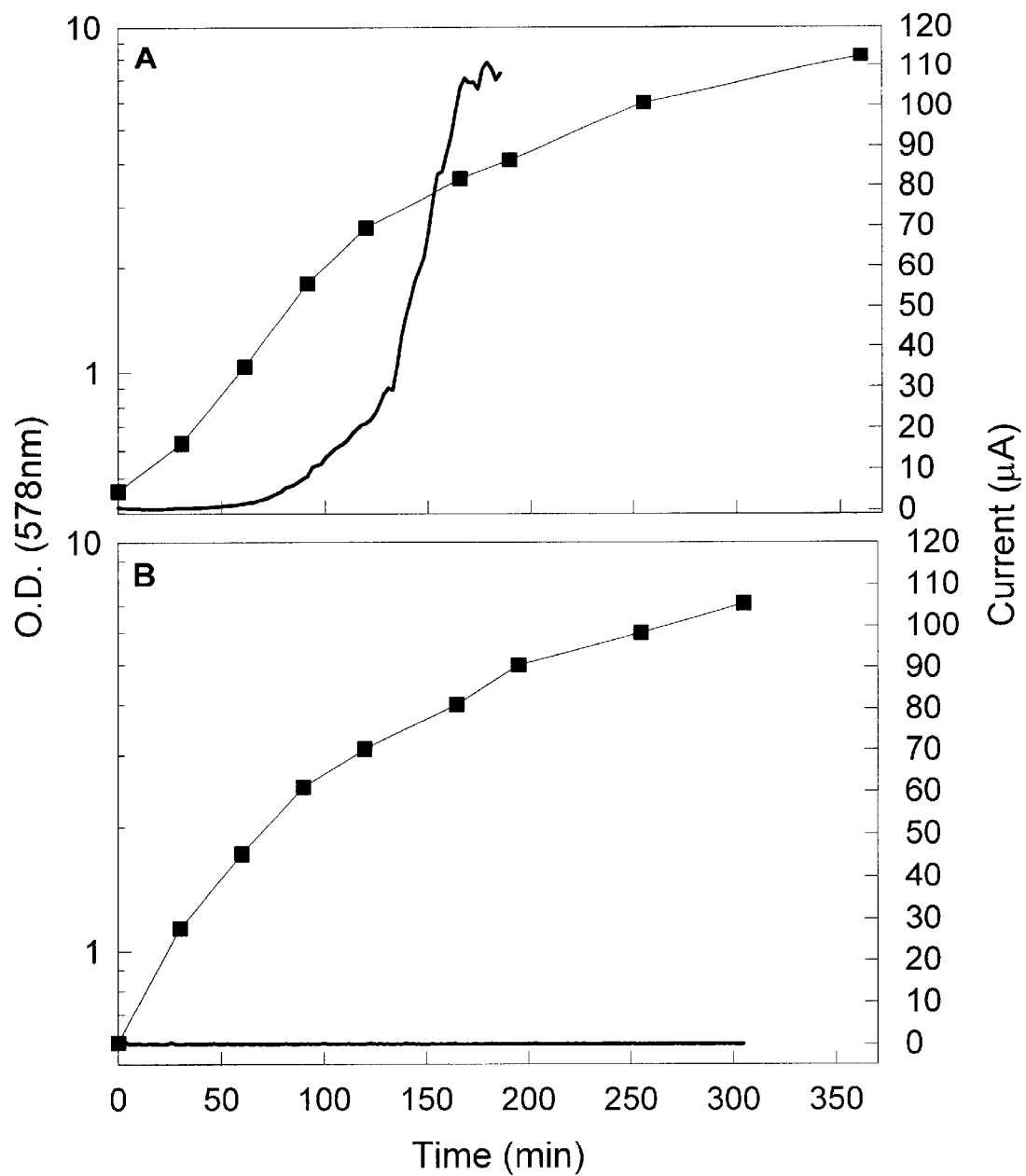
FIGS. 4A–B shows on-line amperometric monitoring of the expression of the osmY-lacZ gene fusion in (A) E. coli strain RO151 (rpoS$^+$) and (B) rpoS mutant E. coli RH99 (rpoS359;;Tn10). The optical density measurement are shown as squares and the amperometric monitoring shows as a continuous line without symbols.

As a model for monitoring gene expression we used *Escherichia E.coli* carrying a chromosomal lacZ fusion to the osmY promoter, which is positively regulated by the transcription factor RpoS ($\sigma^8$) and is therefore expressed only at the stationary phase (Weichart et. al., 1993; Yim & Villarejo, 1992). As a control we used an isogenic strain which carries an interruption of the rpoS gene (Weichart et. al., 1993). In this experiment screen-printed electrodes and graphite working electrode as described above were placed inside the Erlenmeyer flask (see FIG. 1) and the expression of lacZ was continuously measured. As shown in FIG. 4A, the significant increase in the current signal was obtained in the transition of the cells into stationery phase. As seen in FIG. 4B, such a signal was not obtained in the culture of the rpoS mutant strain. These results are in agreement with previous results obtained with a colorimetric assay (Weichart et. al., 1993).

Figure 5:
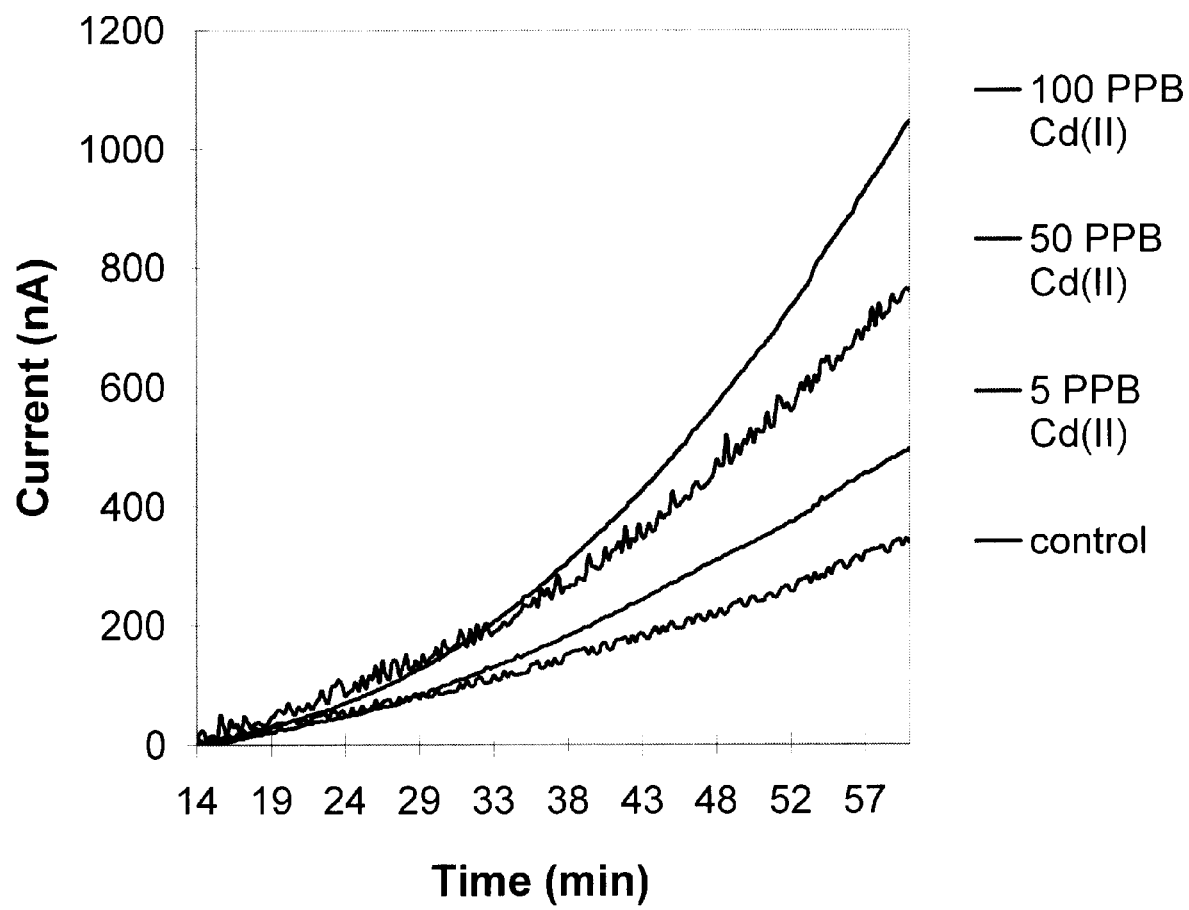
FIG. 5 shows current signal obtained with a biosensor under different cadmium concentrations.

Example 4
On-line Monitoring of Heavy Metals Using Intact Bacteria Carrying a Heavy Metal Responsive Promoter Fused to the Reporter Gene lacZ Coding for the Enzyme β-galactosidase An on-line electroanlytical assays for β-galactosidase was used to monitor on-line the presence of heavy metals. The expression of the reporter gene β-galactosidase that was fused to a heavy metal responsive gene was proportional to the heavy metal concentration. We were able to monitor eight different samples simultaneously using a disposable electrodes. FIG. 5 shows the response of the sensor to elevated (5 PPM, 10 PPM and 50 PPM) concentrations of $CdCl_2$.

In vivo gene fusion was perform using the λplacMu system as previously described. (Sambrook et al., 1989) in order to construct the pollutant-inducible reporting bacteria. *E coli* K12 MC4100 was used and the identification of pollutant responsive mutants was perform by streaking each transposant on MOPS (morpholine-propanessulfonic acid) minimal plates supplemented wit 0.2% glucose and 2 mg $ml^{-1}$ of thiamin containing 50 mg $ml^{-1}$ of kanamycin, 40 mg $ml^{-1}$ of X-gal (5-bromo-4-chloro-3-indolyl-b-D-galactoside) and different pollutant concentrations. The blue colonies were isolated for further examination by a spectrophotometrice assay for β-galactosidase (Sambroet al., 1989). Electrochemical measurements was performed using a disposable three-electrode cell made of polystyrene tubes and based on a screen-printed electrode (total volume of 0.3 ml). The assay was performed directly in the electrochemical cells that was vibrated to achieve mixing. This system allows simultaneous measurements of eight samples using a potentiostat connected to 8 channel multiplexer. The electrical current, resulting in all 8 cultures, from the activity of β-galactosidase, was visualized in real time on the computer screen. The on-line monitoring procedure was performed as followed:

a. The bacteria culture was grown on LB medium to a density of 40 K.U.

b. The culture was added to the multiple-cell device followed by the addition of the β-galactosidase substrate p-aminophenyl-b-D-galactopyranoside (PAPG).

c. A potential of 220 mV Vs Ag/AgCl reference electrode was applied by the electrochemical measurement system and electroanalytical assay for β-galactosidase was carried out as described in Example 4.

d. Heavy metal samples were added and the current signals in each electrochemical cell were visualized on the computer screen and represent the signals from the enzymatic reactions.

The current signal was monitored simultaneously in all the cultures.

As seen in FIG. 5, the slope of the current signals with time was proportional to the concentrations of cadmium added to the culture.

Example 5
On-line Monitoring of Cadmium in Soil Samples

Figure 6:
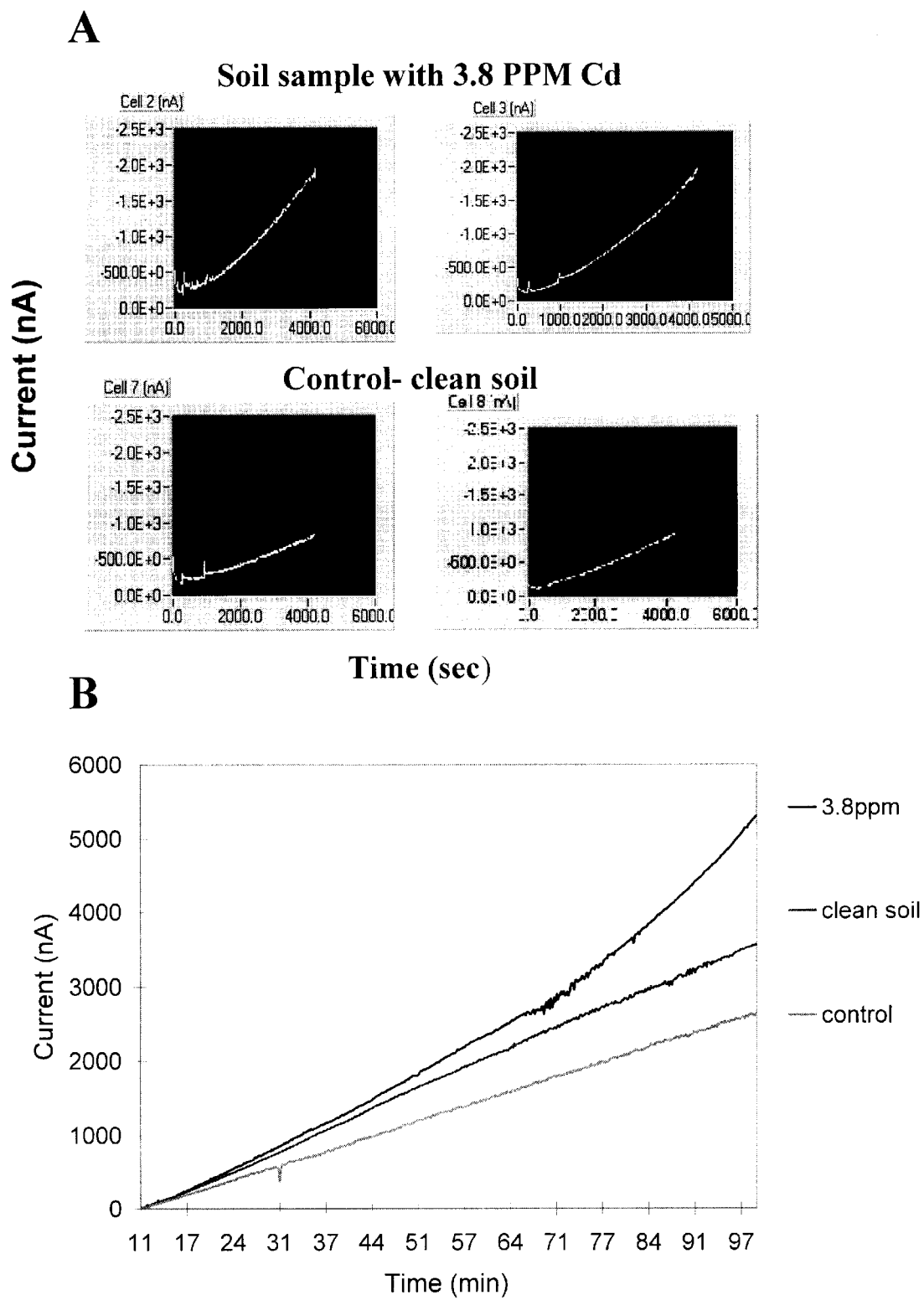
FIGS. 6A–B shows results of determination of cadmium concentration in soil samples containing cadmium (3.8 PPM) versus control clean soil samples: (A) shows the result as seen on a computer screen; (B) shows the processed data.

The same assay procedure was used to detect cadmium in soil samples. The soil was added directly to the screen-printed based electrochemical cells containing the bacteria culture as described above. Eight soil samples were monitored simultaneously by the system. The results as visualized on the computer screen are shown on FIG. 6A., Two duplicates of soil sample containing 3.8 PPM cadmium (measured by the Atomic absorption method) were compared with two duplicates of clean soil samples. Current signals obtained in the soil sample containing 3.8 PPM cadmium were substantially higher than the current signals obtained in the clean soil samples. This can also clearly be seen in FIG. 6B which shows the average data of several experiments of this type, as low as 0.5 PPM cadmium was detected in this soil samples.

Example 6
On-line Monitoring of Mercury in Water and Sea Water Samples

Figure 7:
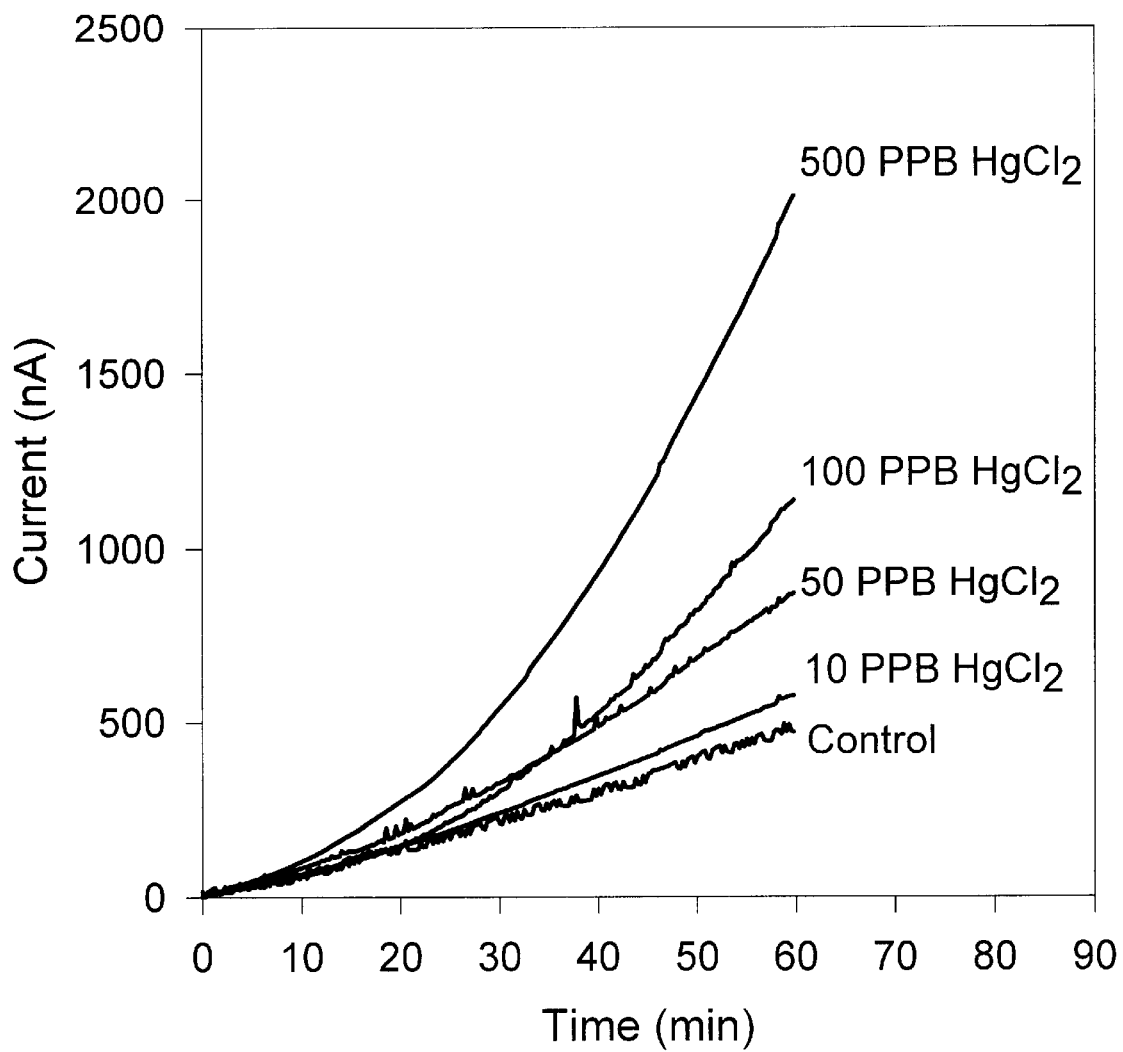
FIG. 7 shows current signal obtained with a biosensor under different mercury concentration in sea-water samples.

The game procedure as described on Example 4 was used to monitor mercury in water and sea water samples. FIG. 7 shows the on-line response of the sensor to elevated (10 PPM, 50 PPM, 100 PPM and 500 PPM) concentrations of $HgCl_2$ that were added to sea-water. The current signal that obtained were proportional to the mercury concentrations and no significant difference was detected between monitoring in water and in sea-water samples.

Example 7
Monitoring of the lacZ Reporter Gene Product β-galactosidase in Intact Yeast Cells The same assay as was described on example 2 was used to monitor the expression of the reporter gene LacZ in yeast cells. The positive control of the yeast two-hybrid system (Groskreutz et. al,, 1997) was used as a model. Tow culture of *Saccharomyces cerevisae* yeast cells strain EGY48 were cotransformed with two hybrid plasmid. One plasmid pS418-34 81exA operator+Lacz reporter) was similar for both cultures. The second plasmid was different, one culture was cotransformed with the plasmid pSH17-4 encoding LexA-GAL4 (a positive control for activation and expression of β-galactosidase) and the second culture was transformed with the plasmid pRFHM-1 encoding LexA-bicoid (a negative control for activation and for repression of β-galactosidase). The cultures were grown on YNB (+GAL, −HIS, −URA) medium for 6 hours.

Figure 8:
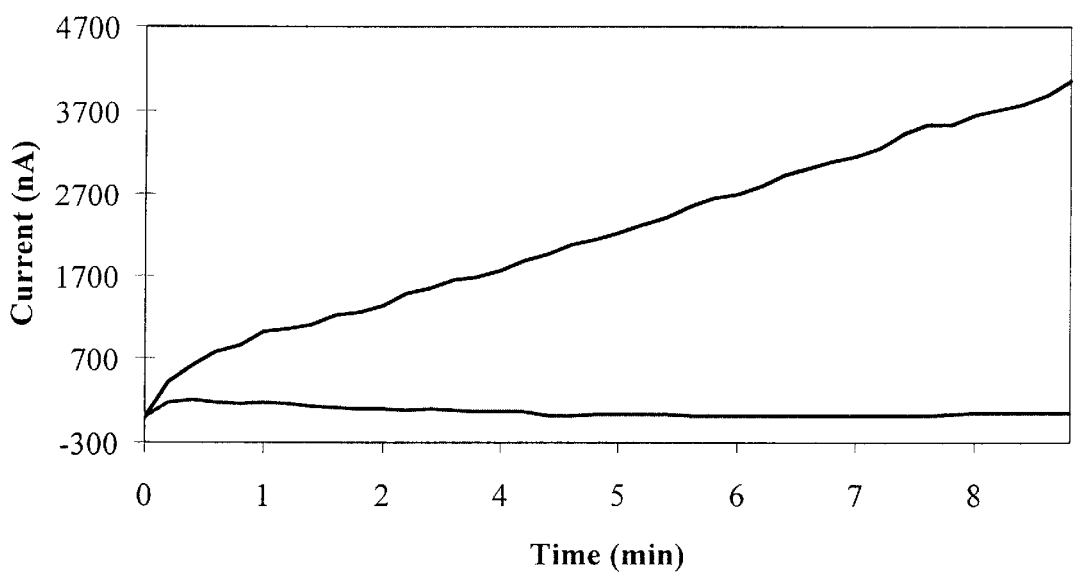
FIG. 8 shows the monitoring of β-galactosidase activity on yeast cells carrying the lacZ reporter gene. The results shows the β-galactosidase activity in yeast cells carrying a plasmid for a positive (high β-galactosidase activity) and a negative (low β-galactosidase activity) controls that are part of the two hybrid system.

Samples were taken from both cultures and were placed in the electrochemical cells. As shown in FIG. 8 a significant difference in current signal were obtained due to different expression levels of β-galactosidase. The strain carrying the plasmid pRFHM-1 expressed as expected a higher level of the enzyme.

Example 8
Monitoring of the lacZ Reporter Gene Product β-galactosidase in Tissue Cultures An on-line electroanlytical assays for β-galactosidase was used to monitor the reporter gene expression in tissue culture.

Figure 9:
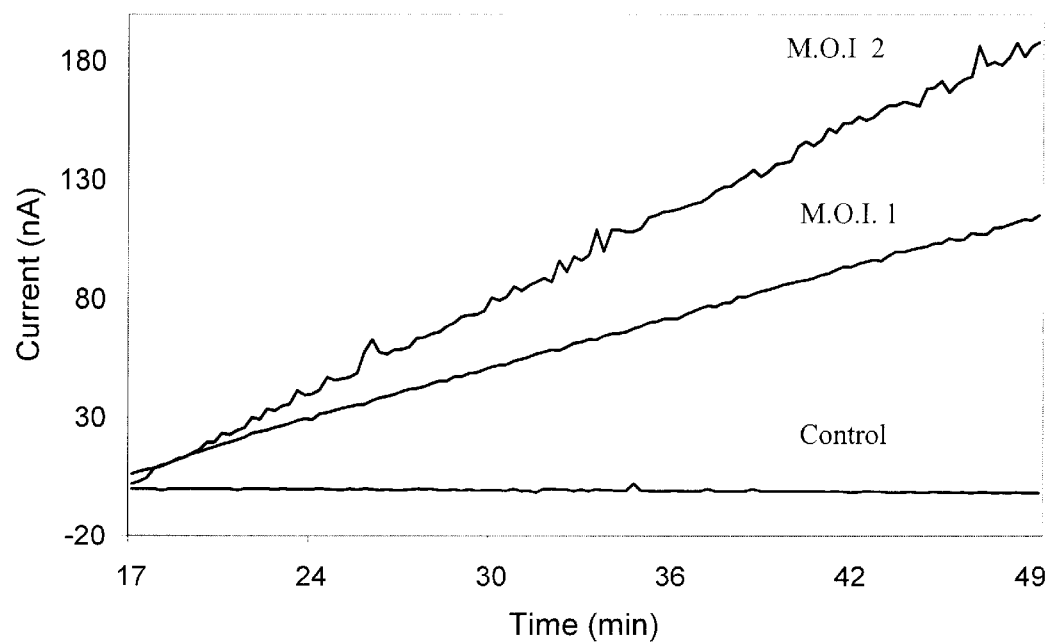
FIG. 9 shows the monitoring of β-galactosidase activity on tissue-cultures that were infected with different MOI of a recombinant MVA virus that express the lacZ reporter gene.

The culture k562 Human erytroleukemia cell line) was divided to 4 cultures each transfected with elevated M.O.I (0, 1, and 2) of the recombinant vaccine virus strain MVA expressing the LacZ gene. All 4 tissue-cultures were grown for 8 hours on the same 6 well plate on standard conditions ($CO_2$ 37° C.). The electrodes (screen-printed and the working graphite) were then placed inside the wells with the tissue-culture. The electrochemical monitoring was performed as described before. As shown in FIG. 9 the current signals obtained were proportional to the M.O.I.

Example 9

Monitoring of the phoA Reporter Gene Product Alkaline Phosphatase (AP) in Intact Bacteria The expression of the enzyme AP was done by constructing a multicopy plasmid. For the construction of the plasmid, we coupled a promoter-less phoA gene to the promoter of the lacZ gene. The use of multicopy plasmid as a vector for induciable genes requires a strong repressing system to prevent constitutive expression. Therefore we used a plasmid that cares the $lacI^q$ gene coding for a lacZ strong repressor. The plasmid was designed to generate the correct fusion between the lacZ promoter and the phoA gene. The bacteria carrying this plasmid can be immobilized and used to monitor AP by electrochemical measurements of it's activity. After the construction of the plasmid, we measured AP activity of a cell suspension in response to the appearance of IPTG.

Figure 10:
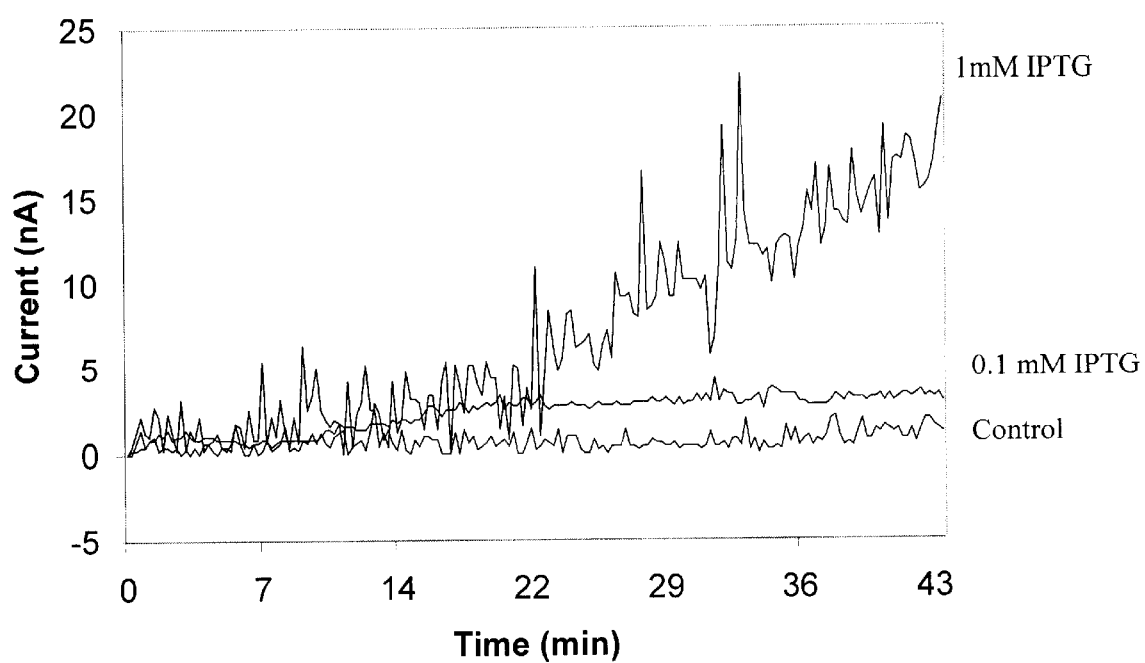
FIG. 10 shows the on-line monitoring of Alkaline phosphatase activity in a recombinant *E. coli* cultures carrying a plasmid with the phoA reporter gene under the promoter of the lacZ gene. The cultures were treated with increasing concentrations of IPTG: (a) no IPTG, (b) 1 mM IPTG, (c) 0.1 mM IPTG. And the on line monitoring of Alkaline phosphatase expression was monitored.

Strain E. coil k-12 7118[F' $lacI^q\Delta$(lacZ)M15 proA+B+/$\Delta$ (lac-proAB) thi supE]was used for all cloning procedures, plasmid propagation and production. AP production of cells carrying the pUC-PhoA plasmid was measured on-line by the electroanalytical technique that was used for β-galactosidase as described in example 2. As shown in FIG. 10 the enzymatic activity was determined following induction with elevated concentrations of IPTG (0, 1 mM and 0.1 mM). By comparing the AP activity in the electrochemical cells we can see that the current signals are proportional to IPTG concentrations.

What is claimed is:

1. A method for detecting a parameter of a host cell, wherein the parameter is:

a nutritional substance;

a substance which regulates cell activity, growth or production of certain substances within the cell;

an external toxic chemical;

a pollutant, or a promoter inducible by external culture conditions, the method comprising:

(a) transfecting said host cell with a plasmid comprising a B-galactosidase or alkaline phosphatase reporter gene under expression control of an inducible promoter sequence, said reporter gene being tolerant to said parameter, said promoter sequence being inducible in correlation with said parameter, said reporter gene encoding an enzymatically active product, said enzymatically active product catalyzing a reaction on p-aminophenyl-B-D-galactopyranoside as a substrate for B-galactosidase, or p-aminophenol-phosphate as a substrate for alkaline phosphatase, which gives rise to an electrical signal, said electrical signal being of sufficient intensity to be monitored by an electrochemical cell, said electrochemical cell comprising a vessel, a measurement electrode, a return electrode, and a reference electrode;

(b) placing the transfected cells in an electrochemical cell; and (c) measuring the level of the electrical signal using the electrochemical cell, wherein a signal above a threshold level indicates the presence of said parameter.

2. A method according to claim 1, wherein said promoter is heterologous to the expressible DNA sequence.

3. A method according to claim 1, wherein said promoter is autologous to the expressible DNA sequence.

4. A method according to claim 1, wherein said promoter is autologous to said host cell.

5. A method according to claim 1, wherein said enzmatically active product is an intracellularly acting enzyme that can catalyze a reaction in which a substrate is converted into a cell membrane-permeable product that can undergo a redox reaction at an electrode of the chemical cell to yield said electrical signal and step (c) comprises adding said substrate to the host cells.

6. A method according to claim 5, wherein said substrate is added to the host cells while in said electrochemical cell.

7. A method according to claim 1, wherein said enzymetically active product is transported out of th cell where it can catalyze a reaction in which a substrate is converted into a reaction product, said product can undergo a redox reaction at an electrode of the chemical cell to yield said electrcal signal and step (c) comprises adding said substrate to the host cells.

8. A method according to claim 7, wherein said substrate is added to the host cells while in said electrochemical cell.

9. A method for determining a parameter in a medium, wherein the parameter is:

a nutritional substance;

a substance which regulates cell activity, growth or production of certain substances within the cell;

an external toxic chemical;

a pollutant; or a substance in the medium, the method comprising:

(a) providing host cells transfected with a plasmid comprising a B-galactosidase or alkaline phosphatase reporter gene under expression control of an inducible promoter sequence, said reporter gene being tolerant to said parameter, said promoter sequence being inducible in correlation with said parameter, said reporter gene encoding an enzymatically active product, said enzymatically active product catalyzing a reaction on p-aminophenyl-B-D-galactopyranoside as a substrate for B-galactosidase, or p-aminophenol-phosphate as a substrate for alkaline phosphatase, which gives rise to an electrical signal, said electrical signal being of sufficient intensity to be monitored by an electrochemical cell, said electrochemical cell comprising a vessel, a measurement electrode, a return electrode, and a reference electrode;

(b) placing said host cells in a medium or sample; and (c) measuring the level of said electrical signal in the medium or sample, the level of said signal being correlated to the level of said parameter.

10. A method according to claim 9, wherein said promoter is heterologous to the expressible DNA sequence.

11. A method according to claim 9, wherein said promoter is autologous to the expressibe DNA sequence.

12. A method according to claims 9, wherein said promoter is autologous to said host cell.

13. A method according to claim 9, wherein said enzymatically active product is an intracellularly acting enzyme that can catalyze a reaction in which a substrate is converted into a cell membrane-permeable product that can undergo a redox reaction at an electrode of the chemical cell to yield said electrical signal and step (c) comprises adding said substrate to the host cells.

14. A method according to claim 13, wherein said substrate is added to the host cells while in said electrochemical cell.

15. A method according to claim 9, wherein said enzymatically active product is transported out of the cell where it can catalyze a reaction in which a substrate is converted into a reaction product, said product can undergo a redox reaction at an electrode of the chemical cell to yield said electrical signal and step (c) comprises adding said substrate to the host cells.

16. A method according to claim 15, wherein said substrate is added to the host cells while in said electrochemical cell.

17. A system for monitoring expression of a target promoter in order to determine a parameter of a host cell, a medium parameter or cell culture growth status indicator parameter, wherein a whole cell assay is used, wherein the parameter is:
   a nutritional substance;
   a substance which regulates cell activity, growth or production of certain substances within the cell;
   an external toxic chemical;
   a pollutant; or
   a substance in the medium,
   the system comprising:
      (a) an electrochemical cell;
      (b) host cells transfected with a plasmid comprising a B-galactosidase or alkaline phosphatase reporter gene under expression control of said target promoter, said reporter gene being tolerant to said parameter, said reporter gene encoding an enzymatically active product, said enzymatically active product catalyzing a reaction on p-aminophenyl-B-D-galactopyranoside as a substrate for B-galactosidase, or p-aminophenol-phosphate as a substrate for alkaline phosphatase, which gives rise to an electrical signal, said electrical signal being of sufficient intensity to be monitored by an electrochemical cell, said electrochemical cell comprising a vessel, a measurement electrode, a return electrode, and a reference electrode; and
      (c) an apparatus for measurement of said electrical signal.

18. A system according to claim 17, comprising a plurality of electrochemical cells and a multiplexing arrangement for an essential simultaneous measurement of the electrical signal from some or all of the cells.

19. A system according to claim 18, comprising an electrode array wherein each electrode contains a different host cell, each host cell comprising a promoter being inducible in correlation with a different parameter.

20. A kit for use in detecting a parameter of a host cell, a medium parameter or cell culture growth status indicator parameter, wherein a whole cell assay is used, wherein the parameter is:
   a nutritional substance;
   a substance which regulates cell activity, growth or production of certain substances within the cell;
   an external toxic chemical;
   a pollutant; or
   a substance in the medium,
   the kit comprising:
      (a) host cells transfected with a plasmid comprising a B-galactosidase or alkaline phosphatase reporter gene under expression control of an inducible promoter sequence, said reporter gene being tolerant to said parameter, said promoter sequence being inducible in correlation with said parameter, said reporter gene encoding an enzymatically active product, said enzymatically active product catalyzing a reaction on p-aminophenyl-B-D-galactopyranoside as a substrate for B-galactosidase, or p-aminophenol-phosphate as a substrate for alkaline phosphatase, which gives rise to an electrical signal, said electrical signal being of sufficient to be monitored by an electrochemical cell;
      (b) at least one component of the electrochemical cell, said electrochemical cell being adapted for receiving and holding the host cells and for performing said electrochemical measurement.

21. A kit according to claim 20, comprising:
   (c) a substrate which is enzymatically reacted on by the enzyme to yield a reaction product giving rise to a redox reaction at an electrode of an electrochemical cell.

22. A method for monitoring of heavy metals in a water, soil or blood sample, comprising:
   (a) adding the sample to an electrochemical cell, wherein the electrochemical cell contains a culture of bacteria expressing a B-galactosidase or alkaline phosphatase reporter gene, said reporter gene being tolerant to the heavy metals and being under expression control of an inducible promoter sequence, said promoter sequence being inducible by said heavy metals, said reporter gene encoding an enzymatically active product, said enzymatically active product catalyzing a reaction on p-aminophenyl-B-D-galactopyranoside as a substrate for B-galactosidase, or p-aminophenol-phosphate as a substrate for alkaline phosphatase, which gives rise to an electrical signal, said electrical signal having sufficient intensity to be monitored by an electrochemical cell;
   (b) performing electrochemical measurements using the electrochemical cell;
   (c) said electrochemical cell comprising a vessel, a measurement electrode, a return cathode and a reference electrode; and
   (d) comparing the results to a standard.

23. The method of claim 22, wherein the heavy metal is cadmium.

24. The method of claim 22, wherein the heavy metal is mercury.

25. The method of claim 22, wherein the water is sea water.

* * * * *

UNITED STATES PATENT AND TRADEMARK OFFICE
CERTIFICATE OF CORRECTION

PATENT NO. : 6,391,549 B1
DATED : May 21, 2002
INVENTOR(S) : Eliora Z. Ron, Judith Rishpon, Israel Biran and Reuven Babai It is certified that error appears in the above-identified patent and that said Letters Patent is hereby corrected as shown below:

Column 14,
Line 8, after "heterologous to the", please replace "expressible DNA sequence" with -- reporter gene --.
Line 10, after "heterologous to the", please replace "expressible DNA sequence" with -- reporter gene --.
Line 23, after "transported out of" and before "cell where it can", replace "th" with -- the --.
Line 63, after "heterologous to the", please replace "expressible DNA sequence" with -- reporter gene --.
Line 65, after "heterologous to the", please replace "expressible DNA sequence" with -- reporter gene --.

Column 16,
Line 21, after "being of sufficient" and before "to be monitored", please insert -- intensity --.
Line 29, before "to yield", please replace "enzyme" with -- enzymatically active product --.

Signed and Sealed this

Twenty-fourth Day of September, 2002

*Attest:*

*Attesting Officer*

JAMES E. ROGAN
*Director of the United States Patent and Trademark Office*